(12) United States Patent
Su et al.

(10) Patent No.: US 8,648,164 B2
(45) Date of Patent: Feb. 11, 2014

(54) LOW-K, FLAME-RETARDANT, BI-FUNCTIONAL BENZOXAZINE AND METHOD FOR MAKING THE SAME

(75) Inventors: Wen-Chiung Su, Taoyuan County (TW); Ching-Hsuan Lin, Taoyuan County (TW); Hung-Tse Lin, Taoyuan County (TW); Feng-Jen Wang, Taoyuan County (TW)

(73) Assignee: Chung-Shan Institute of Science and Technology, Armaments, Bureau, Ministry of National Defense, Taoyuan County (TW)

( * ) Notice: Subject to any disclaimer, the term of this patent is extended or adjusted under 35 U.S.C. 154(b) by 213 days.

(21) Appl. No.: 13/396,891

(22) Filed: Feb. 15, 2012

(65) Prior Publication Data
US 2013/0123457 A1    May 16, 2013

(30) Foreign Application Priority Data

Nov. 10, 2011 (TW) .............................. 100141113 A

(51) Int. Cl.
*C07D 413/10* (2006.01)
*C08G 14/067* (2006.01)
*C08G 14/06* (2006.01)

(52) U.S. Cl.
CPC .............. *C07D 413/10* (2013.01); *C08G 14/06* (2013.01)
USPC ............................................ 528/244; 544/73

(58) Field of Classification Search
None
See application file for complete search history.

(56) References Cited

U.S. PATENT DOCUMENTS

2011/0207908 A1* 8/2011 Su et al. ......................... 528/244
2012/0116078 A1* 5/2012 Lin et al. ......................... 544/73

OTHER PUBLICATIONS

Derwent accession No. 2009-B36737 for Chinese Patent No. 101220152, Lu et al., Jul. 16, 2008, two pages.*

* cited by examiner

*Primary Examiner* — Robert Sellers
(74) *Attorney, Agent, or Firm* — Jackson IPG PLLC

(57) ABSTRACT

Disclosed is a method for making a low-k, flame-retardant, bi-functional benzoxazine. The method includes the steps of dissolving phosphoric diamine with various functional groups, phenolic adamantane and paraformaldehyde in a solvent at 72° C. to 88° C. for 7 to 9 hours, and cooling and introducing the solution in n-hexane to separate the low-k, flame-retardant, phosphoric, bi-functional benzoxazine.

7 Claims, 4 Drawing Sheets

LOW-K, FLAME-RETARDANT, BI-FUNCTIONAL BENZOXAZINE AND METHOD FOR MAKING THE SAME

BACKGROUND OF INVENTION

1. Field of Invention

The present invention relates to a low-k, flame-retardant, bi-functional benzoxazine and, more particularly, to a thermo-stable, flame-retardant, low-k, phosphoric, bi-functional benzoxazine and, more particularly, to a phosphoric benzoxazine with phosphor-oxide bonds made by synthesis of phosphoric diamine.

2. Related Prior Art

Phenolic resin is a common thermosetting resin made by condensation of a phenol monomer and an aldehyde monomer. Benzoxazine is a phenolic resin. By nature, benzoxazine is subjected to ring-opening and curing after it is heated. In comparison with a conventional phenolic resin, benzoxazine exhibits a high glass transition temperature (Tg), a high modulus, low moisture absorption, excellent electric properties, a high char yield, and does not require any catalyst of strong acid, produce any byproducts, or vary in volume during the curing.

Phenolic resin, which is composed of carbon, hydrogen and oxygen, is however easily combustible in use. As the electronic industry develops, electronic products get smaller and lighter. Hence, the pin through hole technology ("PTH") has been replaced with the surface mount technology ("SMT") such as the ball grid array ("BGA"), the flip chip package ("FCP") and the chip size package ("CSP"). Printed circuit boards develop toward high-density and lamination. Moreover, the semiconductor industry gets more and more demanding on the temperature resistance and combustion resistance of materials. For example, all electronic materials must be in compliance with the regulations of UL-94 V-0. There is a trend to pursue flame-retardant electronic materials.

A currently available, flame-retardant benzoxazine includes carbon fibers added therein to improve the combustion resistance. It is however hard to make a flame-retardant, pure benzoxazine, and many efforts have been made to render a polymer flame-retardant. The flame-retardant property of a polymer can be improved by adding alkyen, deoxybenzoin or a phosphoric material therein.

It can be learned from many papers that most bi-functional benzoxazines are made of aromatic bi-sphenol, mono-functional amine monomer and methanol. A benzoxazine made of aromatic bi-sphenol however exhibits poor thermo-stability because its chemical bonds can easily be broken to release aniline at high temperature.

Moreover, it can be learned from many papers that a material of the structure of adamantane exhibits excellent mechanical properties and rigidity for two reasons. Firstly, it exhibits hardness and rigidity. Secondly, it exhibits a low polarity to dilute the influences from the polar structure of a curing material, and this is good for reducing the dielectric constant. It however mainly consists of aliphatic materials and is not flame-retardant.

The present invention is therefore intended to obviate or at least alleviate the problems encountered in prior art.

SUMMARY OF INVENTION

It is an objective of the present invention to provide a low-k, flame-retardant, bi-functional benzoxazine.

It is another objective of the present invention to provide a low-k epoxy curing material by reducing the dielectric constant of benzoxazine and adding the benzoxazine into epoxy ("DGEBA").

To achieve the foregoing objectives, the method includes the steps of dissolving phosphoric diamine with various functional groups, phenolic adamantane and paraformaldehyde in a solvent at 72° C. to 88° C. for 7 to 9 hours, and cooling and introducing the solution in n-hexane to separate the low-k, flame-retardant, phosphoric, bi-functional benzoxazine. The low-k, flame-retardant, phosphoric, bi-functional benzoxazine exhibits a structural formula as follows:

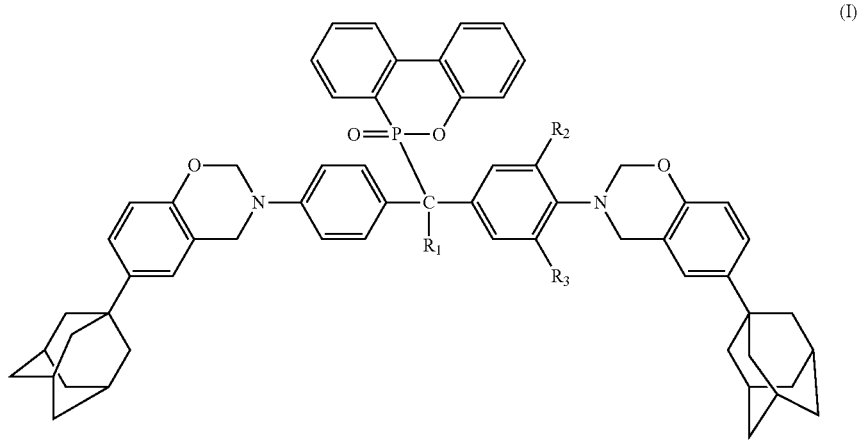

(I)

wherein, R1 to R3 are selected from the group consisting of the hydrogen atom, C1 to C6 alkyl, C3 to C6 naphthene and phenyl.

In the method, the solvent is selected from the group consisting of DMAC/toluene, NMP/toluene, DMSO/toluene, DMAC/xylene, NMP/xylene, DMSO/xylene, ethanol/toluene, ethanol/xylene, methanol/toluene and/or methanol/xylene, wherein toluene or xylene is used as a hydrophobic solvent.

In the method, the phosphoric bi-functional benzoxazine is mixed with the epoxy, i.e., diglycidyl ether bi-sphenol A for copolymerization in molten state without using any solvent, wherein the concentration of the phosphoric bi-functional benzoxazine is 0.1 mole % to 50 mole %.

In the method, the copolymerization temperature is the room temperature to 250° C. and, more particularly, 160° C. to 220° C.

In the method, the copolymerization time is 5 to 24 hours and, more particularly, 6 to 16 hours.

Other objectives, advantages and features of the present invention will be apparent from the following description referring to the attached drawings.

BRIEF DESCRIPTION OF DRAWINGS

The present invention will be described via detailed illustration of the preferred embodiment referring to the drawings wherein.

DETAILED DESCRIPTION OF PREFERRED EMBODIMENT

Figure 1:
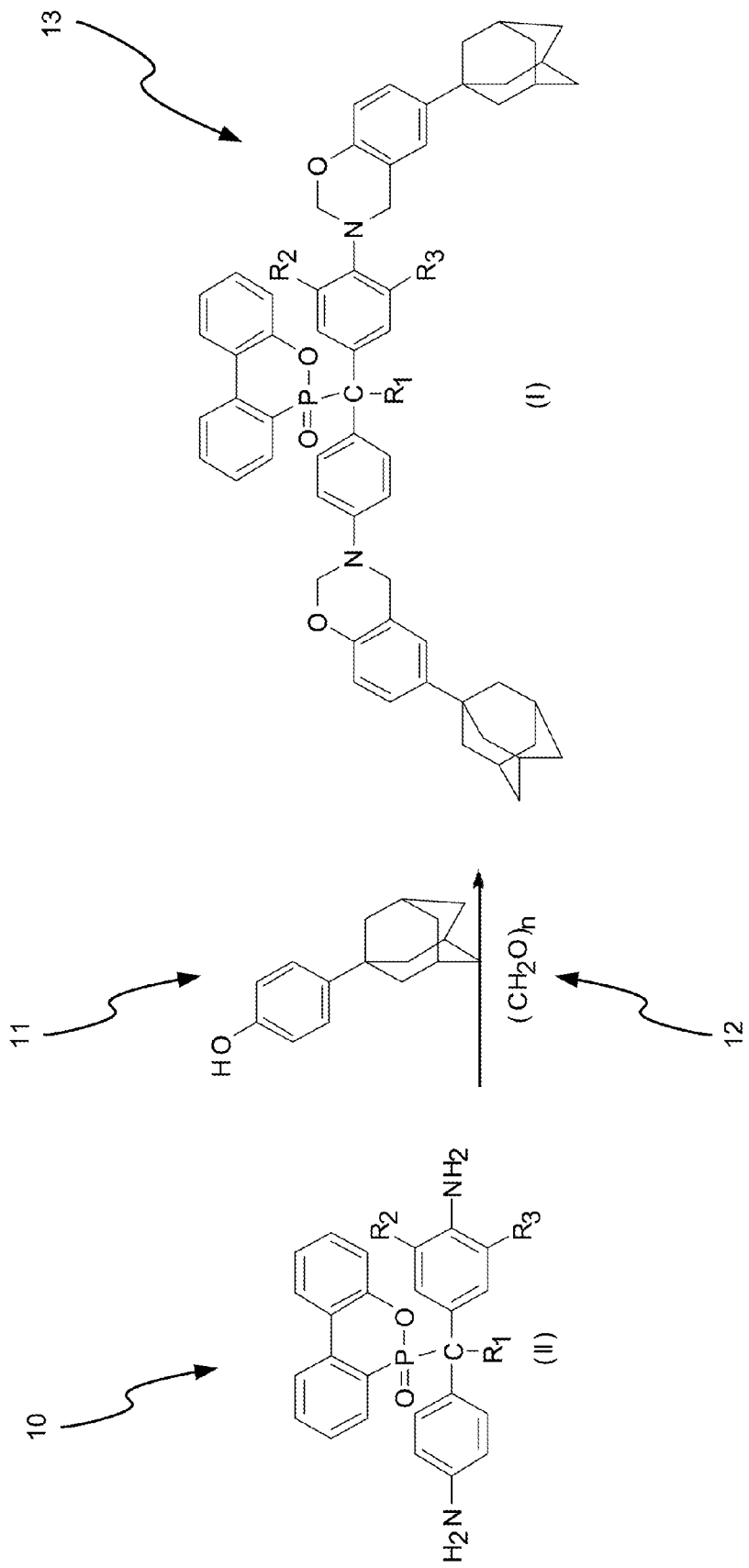
FIG. 1 shows a formula for making a low-k, phosphoric, bi-functional benzoxazine according to the preferred embodiment of the present invention.
Figure 2:
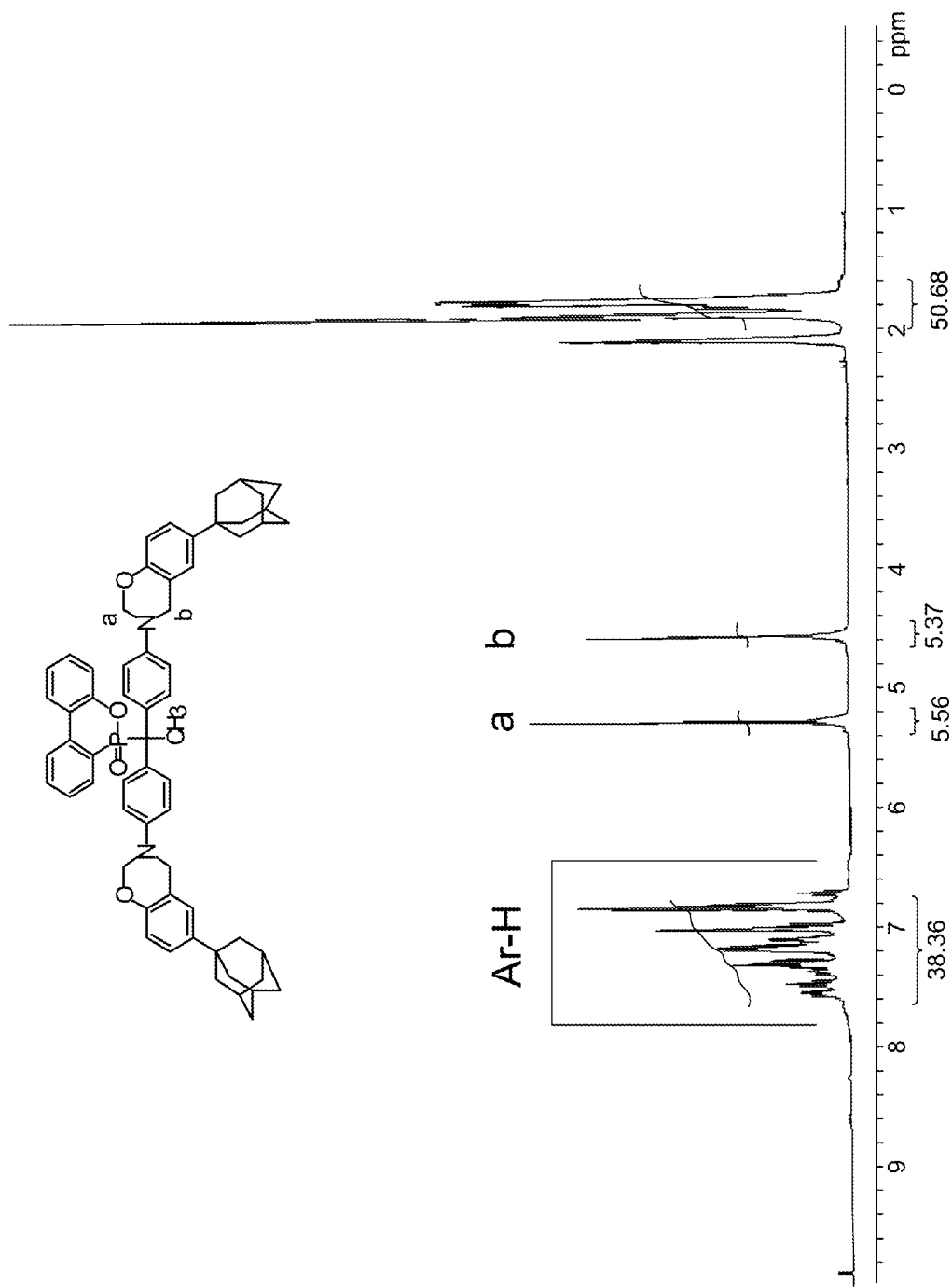
FIG. 2 is a spectrum of a compound I-A in the method shown in FIG. 1.
Figure 3:
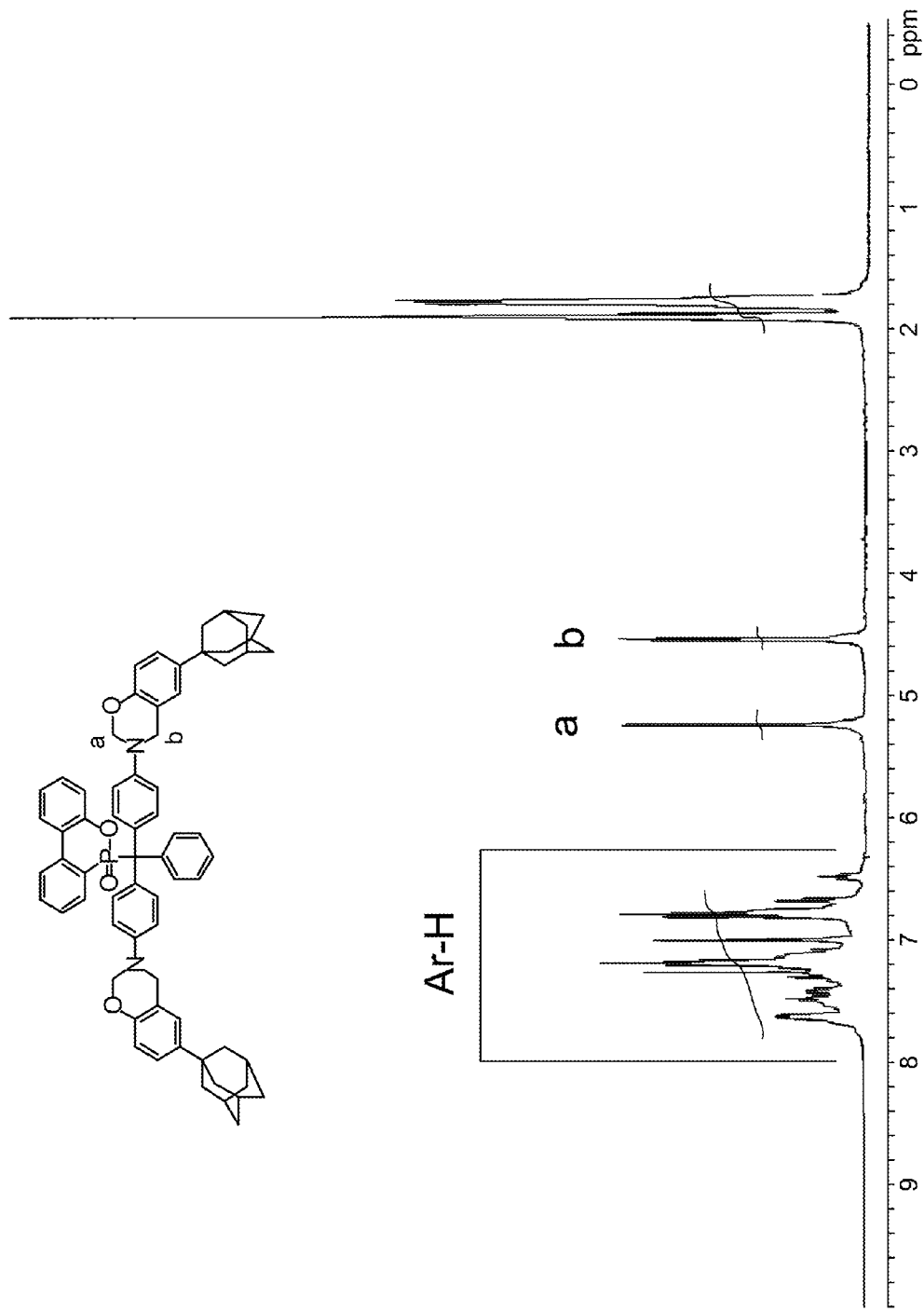
FIG. 3 is a spectrum of another compound I-D in the method shown in FIG. 1.

Referring to FIGS. 1 to 3, there is shown a method for making a low-k, phosphoric, bi-functional benzoxazine according to the preferred embodiment of the present invention. Preferably, a series of low-k, phosphoric, diamines 10 with various functional groups, a phenolic adamantane 11 and methanol 12 are mixed and dissolved in a solvent at 72° C. to 88° C. for 7 to 9 hours to make a low-k, phosphoric, bi-functional benzoxazine 13 that is expressed by structural formula (1):

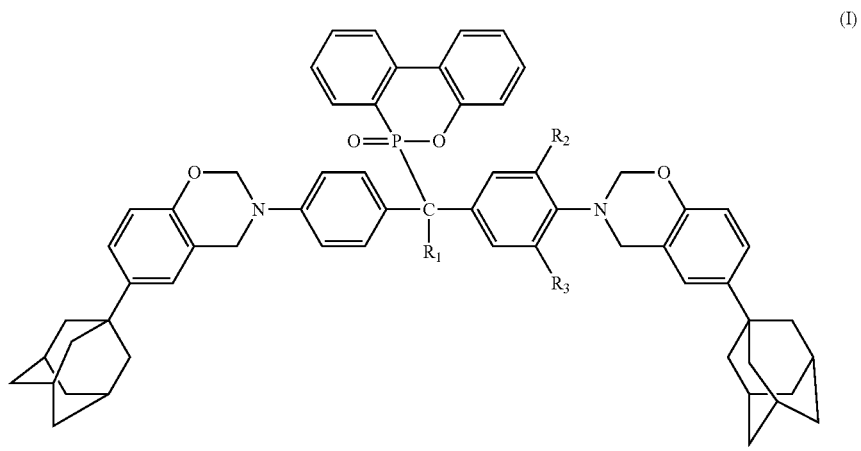

wherein R1 to R3 are selected from the group consisting of hydrogen atom, C1 to C6 alkyl, C3 to C6 benzo-alkyl and phenyl.

The solvent includes DMAC/toluene, NMP/toluene, DMSO/toluene, DMAC/xylene, NMP/xylene, DMSO/xylene, ethanol/toluene, ethanol/xylene, methanol/toluene and/or methanol/xylene. Toluene or xylene is used as a hydrophobic solvent.

Compound I-A

For example, 42.64 grams (0.1 mole) of phosphoric diamine monomer, 45.66 grams (0.2 mole) of phenolic adamantine monomer and 12.01 grams (0.4 mole) of paraformaldehyde are dissolved in ethanol/toluene and stirred at 80° C. for 8 hours. After the reaction system is reduced to the room temperature, the solution is introduced into n-hexane to provide the product in the form of white powder. By suction filtering, the white powder is turned into a filter cake. By drying, the filter cake is turned into 61.45 grams of white powder, compound I-A, at a yield of 66%. Shown in FIG. 2 is a 1H NMR spectrum of the compound I-A.

According to the structural formula (I), R1 can be the methyl group, and R2 and R3 can be compounds of the hydrogen atom, and the compound I-A can be expressed as follows:

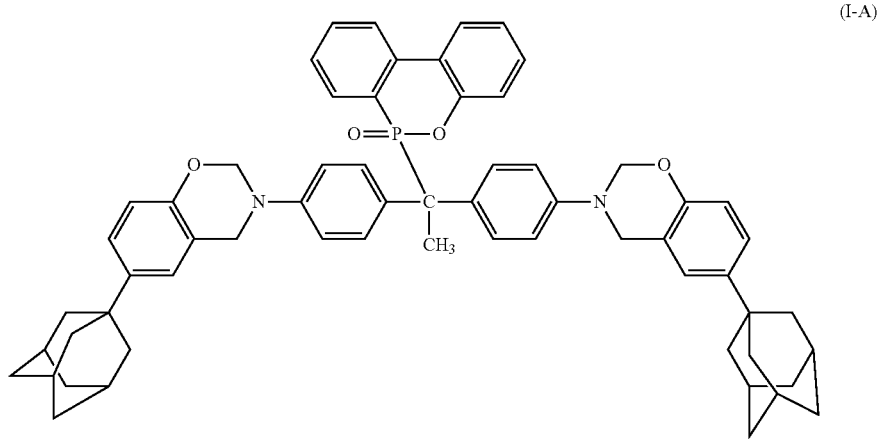 [SMILES: CC(c1ccc(N2COc3ccc(C45CC6CC(CC(C6)C4)C5)cc3C2)cc1)(c1ccc(N2COc3ccc(C45CC6CC(CC(C6)C4)C5)cc3C2)cc1)P1(=O)Oc2ccccc2-c2ccccc21]

(I-A)

Compound I-B

For example, 45.45 grams (0.1 mole) of phosphoric diamine monomer, 45.66 grams (0.2 mole) of phenolic adamantine monomer and 12.01 grams (0.4 mole) of paraformaldehyde are dissolved in ethanol/toluene and stirred at 80° C. for 8 hours. After the reaction system is reduced to the room temperature, the solution is introduced into n-hexane to provide the product in the form of white powder. By suction filtering, the white powder is turned into a filter cake. By drying, the filter cake is turned into 67.51 grams of white powder, compound I-B, at a yield of 70%.

According to the structural formula (I), R1 can be the methyl group, and R2 and R3 can be the methyl group, and the compound I-B can be expressed as follows:

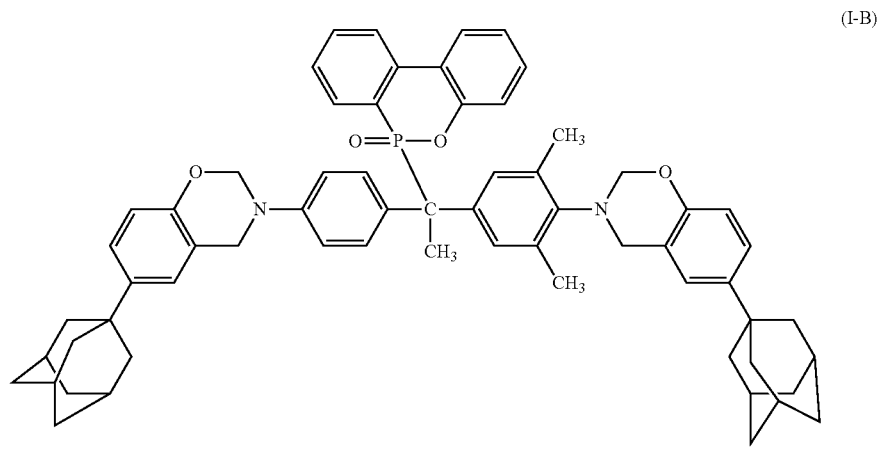 [SMILES: Cc1cc(C(C)(c2ccc(N3COc4ccc(C56CC7CC(CC(C7)C5)C6)cc4C3)cc2)P2(=O)Oc3ccccc3-c3ccccc32)cc(C)c1N1COc2ccc(C34CC5CC(CC(C5)C3)C4)cc2C1]

(I-B)

Compound I-C

For example, 48.25 grams (0.1 mole) of phosphoric diamine monomer, 45.66 grams (0.2 mole) of phenolic adamantine monomer and 12.01 grams (0.4 mole) of paraformaldehyde are dissolved in ethanol/toluene at 80° C. for 8 hours. After the reaction system is reduced to the room temperature, the solution is introduced into n-hexane to provide the product in the form of white powder. By suction filtering, the white powder is turned into a filter cake. By drying, the filter cake is turned into 65.43 grams of white powder, compound I-C, at a yield of 66%.

According to the structural formula (I), R1 can be the methyl group, and R2 and R3 can be ethyl, and the compound I-C can be expressed as follows:

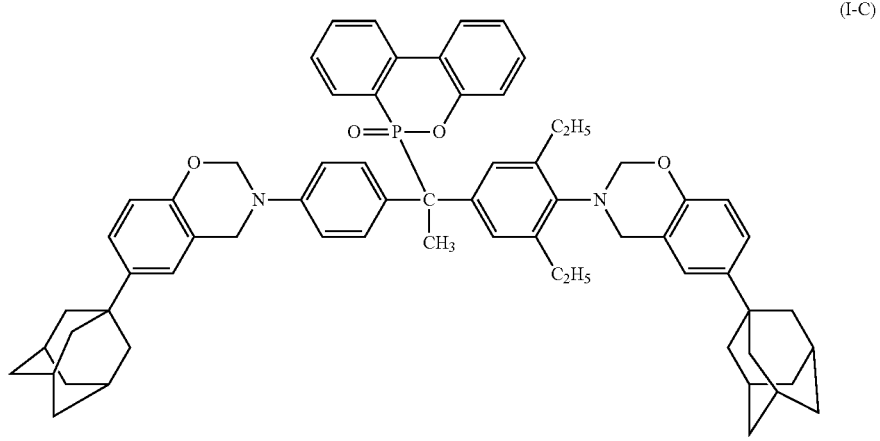 [SMILES: CCc1cc(C(C)(c2ccc(N3COc4ccc(C56CC7CC(CC(C7)C5)C6)cc4C3)cc2)P2(=O)Oc3ccccc3-c3ccccc32)cc(CC)c1N1COc2ccc(C34CC5CC(CC(C5)C3)C4)cc2C1]

(I-C)

Compound I-D

For example, 48.85 grams (0.1 mole) of phosphoric diamine monomer, 45.66 grams (0.2 mole) of phenolic adamantine monomer and 12.01 grams (0.4 mole) of paraformaldehyde are dissolved in ethanol/toluene and stirred at 80° C. for 8 hours. After the reaction system is reduced to the room temperature, the solution is introduced into n-hexane to provide the product in the form of white powder. By suction filtering, the white powder is turned into a filter cake. By drying, the filter cake is turned into 57.6 grams of white powder, compound I-D, at a yield of 58%. Shown in FIG. 3 is a 1H NMR spectrum of the compound I-D.

According to the structural formula (I), R1 can be phenyl, R2 and R3 can be compounds of the hydrogen atom, and the compound I-D can be expressed as follows:

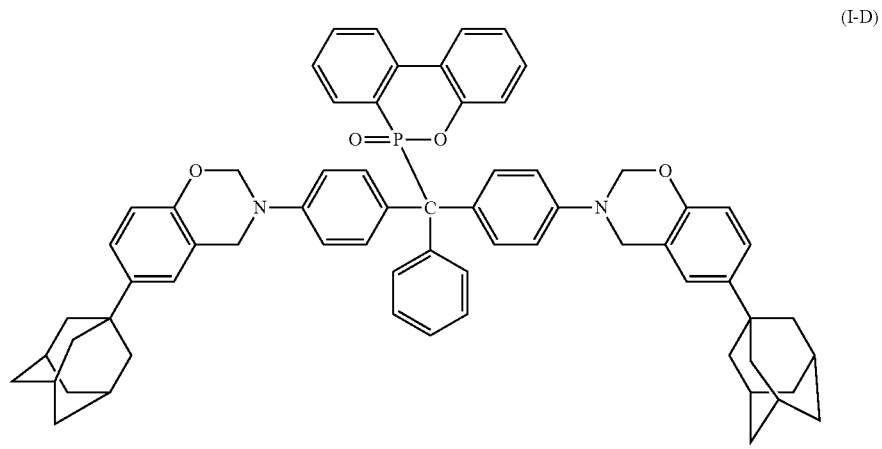 [SMILES: O=P1(C(c2ccccc2)(c2ccc(N3COc4ccc(C56CC7CC(CC(C7)C5)C6)cc4C3)cc2)c2ccc(N3COc4ccc(C56CC7CC(CC(C7)C5)C6)cc4C3)cc2)Oc2ccccc2-c2ccccc21]

(I-D)

Compound I-E

For example, 51.65 grams (0.1 mole) of phosphoric diamine monomer, 45.66 grams (0.2 mole) of phenolic adamantine monomer and 12.01 grams (0.4 mole) of paraformaldehyde are dissolved in ethanol/toluene and stirred at 80° C. for 8 hours. After the reaction system is reduced to the room temperature, the solution is introduced into n-hexane to provide the product in the form of white powder. By suction filtering, the white powder is turned into a filter cake. By drying, the filter cake is turned into 68.51 grams of white powder, compound I-E, at a yield of 67%.

According to the structural formula (I), R1 can be phenyl, and R2 and R3 can be the methyl group, and the compound I-E can be expressed as follows:

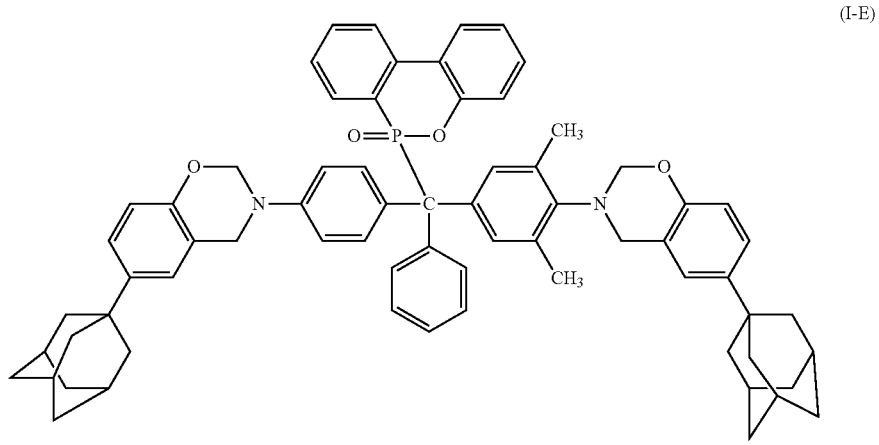 [SMILES: Cc1cc(C(c2ccccc2)(c2ccc(N3COc4ccc(C56CC7CC(CC(C7)C5)C6)cc4C3)cc2)P2(=O)Oc3ccccc3-c3ccccc32)cc(C)c1N1COc2ccc(C34CC5CC(CC(C5)C3)C4)cc2C1]

(I-E)

Compound I-F

For example, 54.46 grams (0.1 mole) of phosphoric diamine monomer, 45.66 grams (0.2 mole) of phenolic adamantine monomer and 12.01 grams (0.4 mole) of paraformaldehyde are dissolved in ethanol/toluene and stirred at 80° C. for 8 hours. After the reaction system is reduced to the room temperature, the solution is introduced into n-hexane to provide the product in the form of white powder. By suction filtering, the white powder is turned into a filter cake. By drying, the filter cake is turned into 69.43 grams of white powder, compound I-E, at a yield of 66%.

Figure 4:
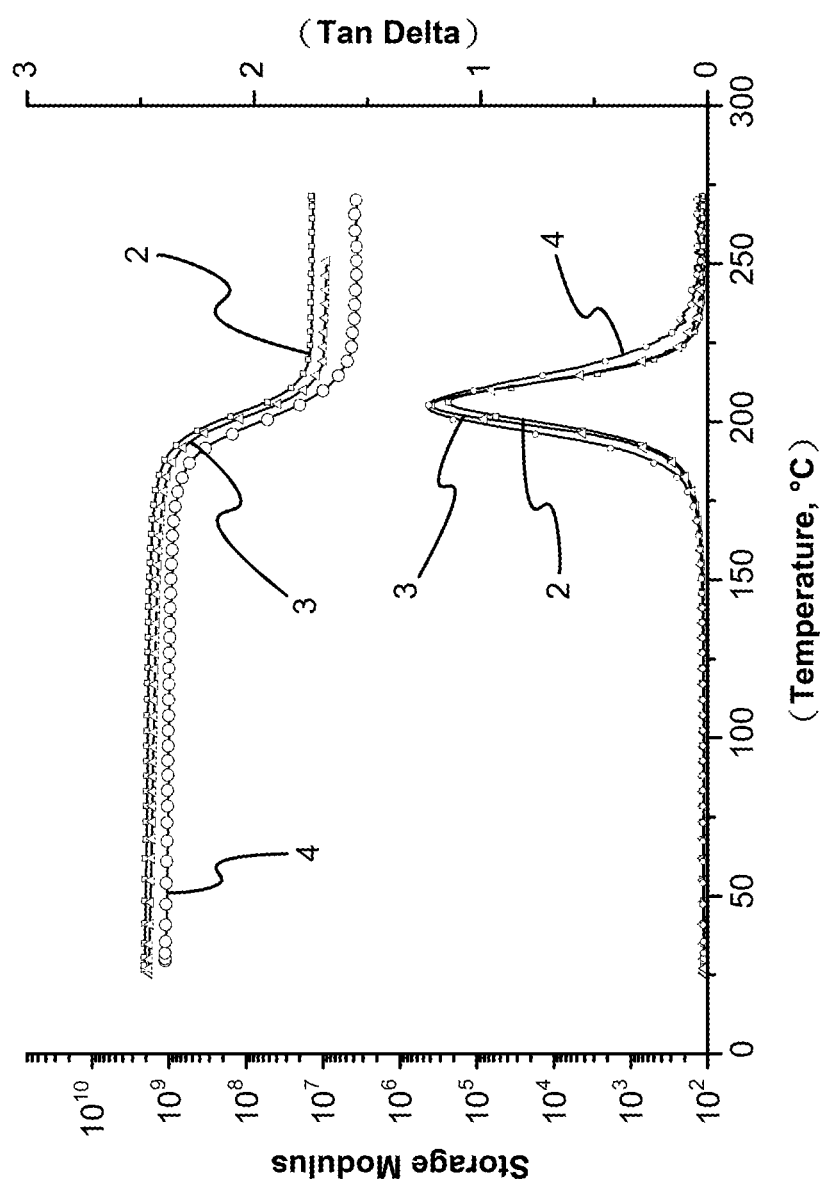
FIG. 4 is a chart of several mechanical properties of the compound I-A versus the phosphoric concentration.

According to the structural formula (I), R1 can be phenyl, and R2 and R3 can be ethyl, and the compound I-F can be expressed as follows:

Shown in FIG. 4 are several mechanical properties of the compound I-A versus the phosphoric concentration. Without the use of any solvent, 0.1 mole % to 50 mole % of phosphoric bi-functional benzoxazine can be added into the benzoxazine monomer and then mixed with epoxy such as bi-sphenol A diglycidyl ether bi-sphenol A, ("DGEBA") for copolymerization in a molten state. The temperature of the resultant copolymer is the room temperature to 250° C. and, preferably, 160° C. to 220° C. The time of the copolymerization is 5 to 24 hours and, preferably, 6 to 16 hours.

Based on different reactants, i.e., the benzoxazine and epoxy, epoxy curing materials are made with various properties. The properties of the curing materials are listed in Table 1. Listed in Table 1 are the dielectric constants of the epoxy curing materials made of the compounds I-A and I-D. The dielectric constant test is focused on the ability of the tested pieces of the epoxy curing materials to interfere with the transmission of signals in an electronic device.

Referring to Table 1 and FIG. 4, as the benzoxazine monomer, epoxy (DGEBA) and co-curing material (4,4'-Diaminodiphenylsulfone, DDS) are mixed and cured, the dielectric constant considerably drops, and the glass transition temperature gets better.

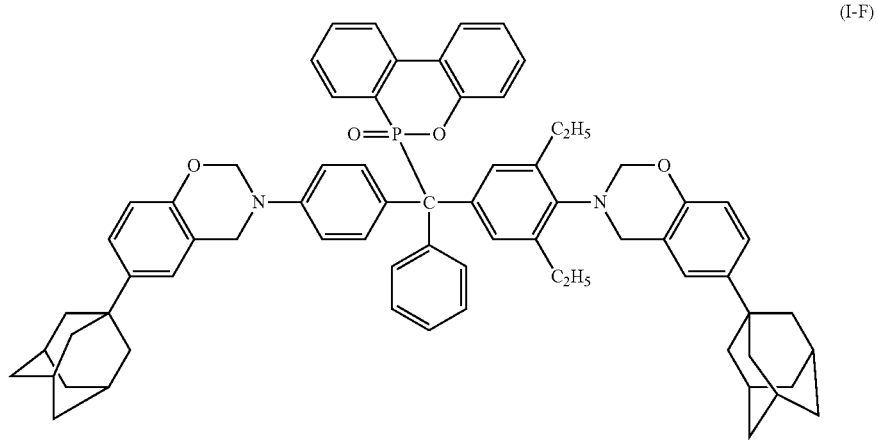 [SMILES: CCc1cc(C(c2ccccc2)(c2ccc(N3COc4ccc(C56CC7CC(CC(C7)C5)C6)cc4C3)cc2)P2(=O)Oc3ccccc3-c3ccccc32)cc(CC)c1N1COc2ccc(C34CC5CC(CC(C5)C3)C4)cc2C1]

(I-F)

TABLE 1

| | P (wt %) | $D_K(U)$ 100 MH$_z$ | 1 GH$_z$ | $D_f$(mU) 100 MH$_z$ | 1 GH$_z$ |
|---|---|---|---|---|---|
| DGEBA | 0 | 3.45 ± 0.07 | 3.39 ± 0.004 | 8.81 ± 0.4 | 8.51 ± 0.06 |
| (I-A)/ DGEBA | 0.5 | 2.74 ± 0.04 | 2.70 ± 0.005 | 8.397 ± 0.6 | 7.838 ± 0.05 |
| (I-A)/ DGEBA | 1.0 | 2.87 ± 0.05 | 2.86 ± 0.005 | 8.428 ± 0.7 | 7.956 ± 0.05 |
| (I-A)/ DGEBA | 1.5 | 2.99 ± 0.08 | 2.94 ± 0.005 | 8.463 ± 0.5 | 7.971 ± 0.05 |

TABLE 1-continued

| | P (wt %) | $D_K(U)$ 100 MH$_z$ | 1 GH$_z$ | $D_f(mU)$ 100 MH$_z$ | 1 GH$_z$ |
|---|---|---|---|---|---|
| (I-D)/ DGEBA | 0.5 | 3.07 ± 0.02 | 2.83 ± 0.005 | 8.336 ± 0.4 | 8.105 ± 0.05 |
| (I-D)/ DGEBA | 1.0 | 3.11 ± 0.06 | 2.98 ± 0.005 | 8.593 ± 0.5 | 8.491 ± 0.05 |
| (I-D)/ DGEBA | 1.5 | 3.17 ± 0.07 | 3.12 ± 0.005 | 8.839 ± 0.7 | 8.749 ± 0.05 |

Listed in Table 2 are the flame-retardations of the epoxy curing materials made of the compounds I-A and I-F. As the benzoxazine monomer, epoxy (DGEBA) and co-curing material (DDS) are mixed and cured, the time of combustion considerably drops, i.e., the curing material flame-retardation increases as the concentration of phosphor increases.

TABLE 2

| Thermoset ID | P (wt %)$^a$ | $t_1$ (sec)$^b$ | $t_2$ (sec)$^c$ | UL-94 Rating |
|---|---|---|---|---|
| (I-A)/DGEBA/DDS | 0.5 | 22.7 | 6.3 | V-1 |
| (I-A)/DGEBA/DDS | 1.0 | 15.2 | 4.1 | V-1 |
| (I-A)/DGEBA/DDS | 1.5 | 5.4 | 3.3 | V-0 |
| (I-F)/DGEBA/DDS | 0.5 | 21.3 | 3.5 | V-1 |
| (I-F)/DGEBA/DDS | 1.0 | 16.3 | 3.6 | V-1 |
| (I-F)/DGEBA/DDS | 1.5 | 5.5 | 2.5 | V-0 |

In Table 2, "a" represents the concentration of phosphor, "b" represents the first average flame time, and "c" represents the second average flame time.

Shown in FIG. 4 are several mechanical properties of the I-A curing materials that contain various proportions of phosphor of 0.5, 1.0 and 1.5 represented by curves 2, 3 and 4. The curves in an upper portion of the chart represent the storage moduli of the specimens benchmarked against the left vertical coordinate axis. The curing materials stand different stresses at different temperatures. The peaks of the curves in a lower portion of the chart represent the glass transition temperatures of the specimens benchmarked against the right vertical coordinate axis. That is, the curing materials stand higher operative temperatures as the glass transition temperatures increase.

Referring to FIG. 4, the benzoxazine/epoxy curing materials exhibit high glass transition temperatures for operation at 150° C. to 220° C. Moreover, the benzoxazine/epoxy curing materials exhibit excellent mechanical properties.

The method of the present invention exhibits the following advantages:

At first, it is a new approach to the reduction of the dielectric constant of benzoxazine and successful introduction of benzoxazine into epoxy to provide a low-k epoxy curing material.

Secondly, the method is simple for including only one step, and can be executed conveniently in mass production.

Thirdly, the curing materials made of the phosphoric bi-functional benzoxazine exhibit excellent mechanical properties, thermo-stability, low dielectric constants and low variation in size.

The present invention has been described via the detailed illustration of the preferred embodiment. Those skilled in the art can derive variations from the preferred embodiment without departing from the scope of the present invention. Therefore, the preferred embodiment shall not limit the scope of the present invention defined in the claims.

The invention claimed is:

1. A method for making a low-k, flame-retardant, bi-functional benzoxazine including the steps of:
   dissolving phosphoric diamine with various functional groups, phenolic adamantane and paraformaldehyde in a solvent at 72° C. to 88° C. for 7 to 9 hours; and
   cooling and introducing the solution in n-hexane to separate the low-k, flame-retardant, phosphoric, bi-functional benzoxazine that exhibits a structural formula as follows:

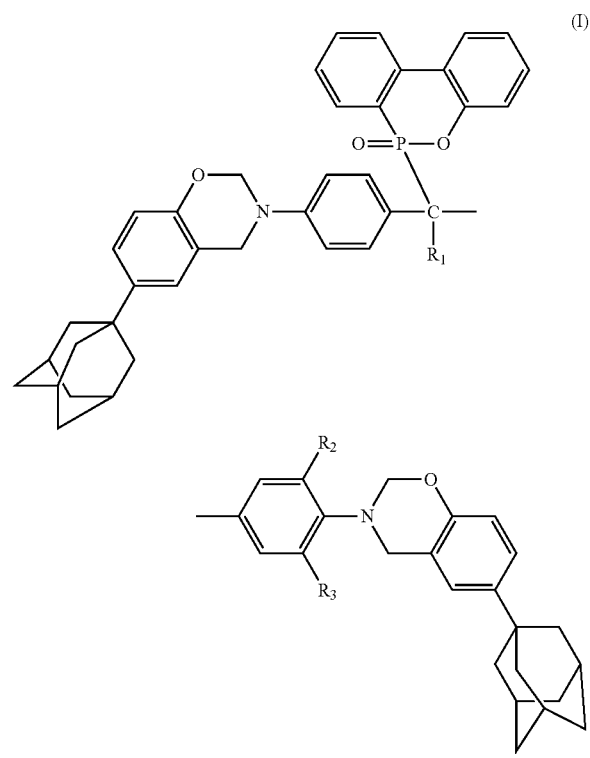

wherein, R1 to R3 are selected from the group consisting of the hydrogen atom, C1 to C6 alkyl, C3 to C6 naphthene and phenyl.

2. The method according to claim 1, wherein the solvent is selected from the group consisting of DMAC/toluene, NMP/toluene, DMSO/toluene, DMAC/xylene, NMP/xylene, DMSO/xylene, ethanol/toluene, ethanol/xylene, methanol/toluene and/or methanol/xylene, wherein toluene or xylene is used as a hydrophobic solvent.

3. The method according to claim 1, wherein the phosphoric bi-functional benzoxazine is mixed with the epoxy, i.e., diglycidyl ether bi-sphenol A for copolymerization in molten state without using any solvent, wherein the concentration of the phosphoric bi-functional benzoxazine is 0.1 mole % to 50 mole %.

4. The method according to claim 3, wherein the copolymerization temperature is the room temperature to 250° C.

5. The method according to claim 3, wherein the copolymerization temperature is 160° C. to 220° C.

6. The method according to claim 3, wherein the copolymerization time is 5 to 24 hours.

7. The method according to claim 3, wherein the copolymerization time is 6 to 16 hours.

* * * * *